United States Patent [19]

Jung

[11] Patent Number: 5,351,680
[45] Date of Patent: Oct. 4, 1994

[54] SURGICAL RETRACTOR

[76] Inventor: Hong I. Jung, 1416 Monroe Ave., Dunmore, Pa. 18509

[21] Appl. No.: 33,182

[22] Filed: Mar. 16, 1993

Related U.S. Application Data

[63] Continuation of Ser. No. 783,538, Oct. 28, 1991, abandoned.

[51] Int. Cl.$^5$ .............................................. A61B 17/02
[52] U.S. Cl. ...................................... 128/20; D24/135
[58] Field of Search .............. 128/20, 3, 15; D24/133, D24/135

[56] References Cited

U.S. PATENT DOCUMENTS

| | | | |
|---|---|---|---|
| 659,182 | 10/1900 | Pilling | 128/20 |
| 1,465,259 | 8/1923 | Friedman | 128/20 |
| 2,863,444 | 12/1958 | Winsten | 128/20 |
| 3,651,800 | 3/1972 | Wilbanks | 128/20 X |
| 4,610,243 | 9/1986 | Ray | 128/20 |

OTHER PUBLICATIONS

Truax Greene & Co. Catalog, 1893, p. 1477.
Murray Baumgartner Surgical Instrument Co. Catalog, 1934, p. 113.

Primary Examiner—Richard J. Apley
Assistant Examiner—Karen A. Jalbert
Attorney, Agent, or Firm—Richard R. Mybeck

[57] ABSTRACT

The present invention is a novel surgical retractor used singularly or in pairs to provide optimum viewing exposure of the surgical field during open gallbladder and biliary tract surgery and to assist in the closing. This stainless steel device comprises a broad rectangular head portion, a narrow angular neck portion, a flat body portion and a flat tail portion disposed angularly relative to the central longitudinal axis of the body portion. The angular relationship between the tail portion and the central longitudinal axis of the body portion will be from about 20° to about 30° in one embodiment of the retractor and from about 75° to about 95° in a second embodiment of the retractor. The device is useful in a small incision thus reducing operation time and cost while improving patient safety and recovery time.

10 Claims, 2 Drawing Sheets

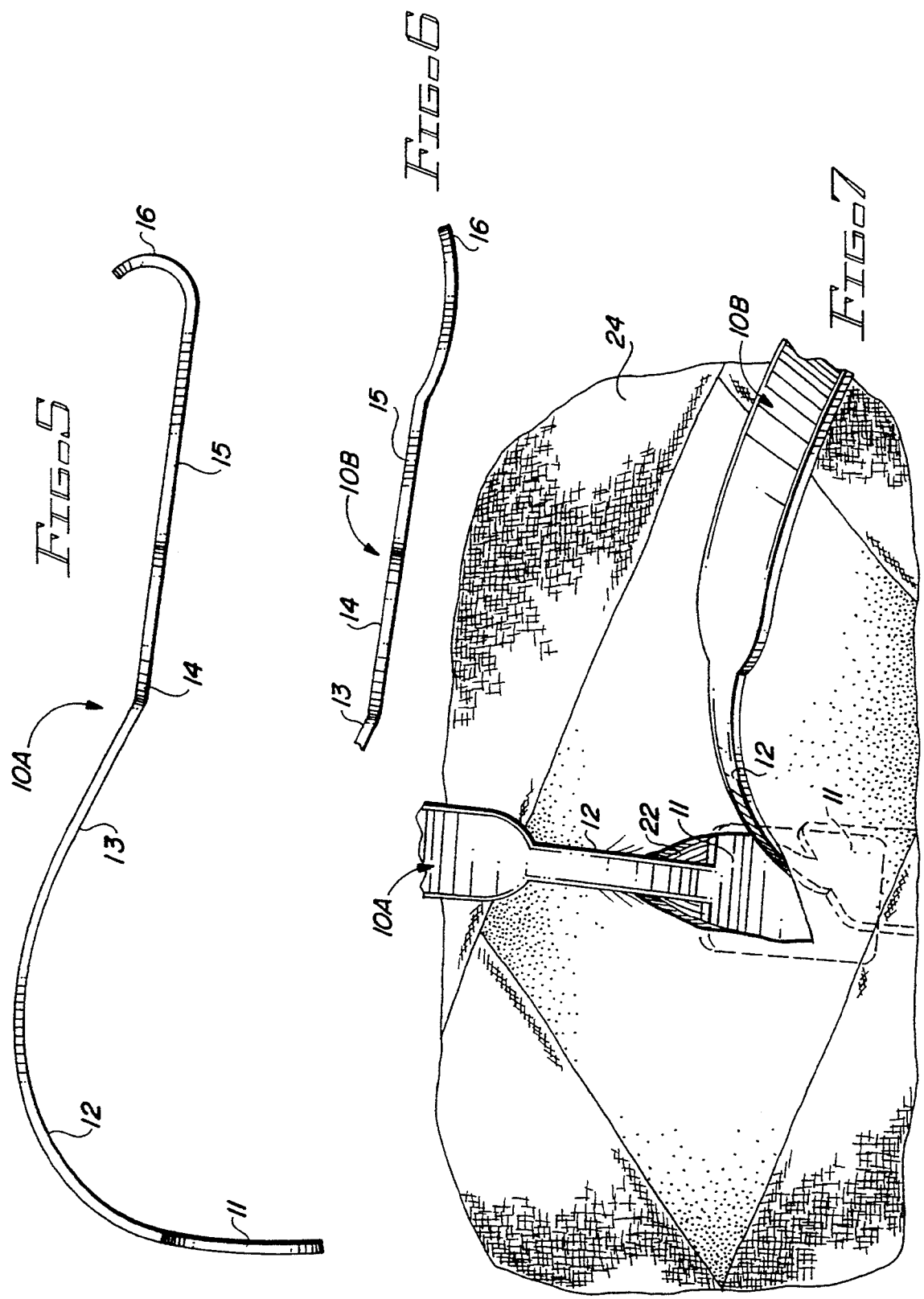

SURGICAL RETRACTOR

This is a continuation application from Ser. No. 07/783,538 filed Oct. 28, 1991 now abandoned.

The present invention relates generally to a surgical retractor and more particularly to a new and improved minicholecystectomy retractor for performing safe open gallbladder and biliary tract surgery and achieves complete exposure of the cysto-hepatic area, Triangle of Calot and Moosman's area.

BACKGROUND OF THE INVENTION

Because of crowded anatomic arrangement and normal variation in anatomic structures in the human cysto-hepatic area, complete direct visual exposure is vital during open surgery to correctly identify and perform a delicate dissection or the restructuring of organs disposed therein. Prior art solutions included solutions to the basic need of exposing the required areas for surgery, but each had serious problems associated with them as will be hereinafter described.

The more commonly used retractor instruments used for cholecystectomy procedures do not provide an optimum view of the operational area because the device itself obscures the surgeon's direct view into the opening. For example, Ray (U.S. Pat. No. 4,610,243) describes a flat, uniform width force-fulcrum retractor which has at least one "spike" affixed to one end of the band. Since the width is uniform along the body portion, no convenient grip segment is available to aid in the insertion. In use, the spike end is embedded in a suitable bone, the retractor is shaped to the general shape required and the natural resilience of the retractor material provides the necessary force to separate the surrounding tissue from the center of the incision. (See: Ray, col. 1, lines 58-63)

Another retractor is described by Pilling (U.S. Pat. No. 659,182). This retractor has a concave head and neck portion which offers little or no resilience, therefore it is not suitable for reforming to use in a specific incisional opening. In addition, the head and tail portions are bent at about the same angle from the body portion, limiting the applications of use.

Wilbanks (U.S. Pat. No. 3,651,800) teaches a retractor in which the shank portion merges into a bowl or spoon shaped portion. (See: Wilbanks, col. 2, lines 17-19) The head, neck and body portions are concave, cylindrical segments which, as in Pilling, detracts from the resilience force necessary in small incision surgery.

Commonly, cholecystectomy retractors had a wide head and a long, wide neck portion which occupied a large portion of the surgical incision defined when attempting to expose the cysto-hepatic area around the gallbladder. Thus, in order to achieve an adequate viewing area, the instruments required an extraordinarily long incisional opening. This resulted in longer operation times, increased costs of surgery and extended patient recovery times.

SUMMARY OF THE INVENTION

The present invention comprises a novel and unique medical retractor device capable of providing maximum vision of the surgical field through a small skin incision, thereby aiding in the dissection of the vascular and the ductal structures during gallbladder and biliary tract surgery. The present invention comprises a stainless steel retractor having a broad portioned head, narrow neck, slender body with a narrowed finger grip and a tail, measuring a total length of 25 cm.

Because of its unique and novel structure, a direct visual exposure of the surgical field is achieved when using the present invention in a small incision; thus, solving the inherent problems of the prior art, and the long incisional wounds associated therewith.

Accordingly, it is a principal object of the present invention to provide a device that solves in a unexpected and unique fashion, all of the aforementioned problems associated with prior art surgical separators, while providing an efficient instrument to help insure a safe cholecystectomy.

Another object of the present invention is to provide a unique and novel surgical retractor which, when used in a small incision, achieves complete exposure of the cysto-hepatic area, Triangle of Calot and Moosman's area.

A further object of the present invention is to provide a novel and unique surgical retractor for assisting in cholecystectomy and biliary tract surgery with significantly less invasiveness than heretofore obtainable with prior art devices.

Still another object of the present invention is to provide a novel and unique surgical retractor which, with minimal invasiveness provides a maximized viewing exposure of cysto-hepatic area, Triangle of Calot and Moosman's area around the gallbladder to facilitate the delicate dissection of the vascular and the ductal structures during gallbladder and biliary tract surgery.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

BRIEF DESCRIPTION OF THE DRAWINGS

In the drawings:

FIG. 5 is a side elevation of the surgical retractor of FIG. 1;

FIG. 6 is a side elevation of the surgical retractor of FIG. 2;

FIG. 7 is a cut-away view showing how retractors embodying the present invention are used to provide an adequate working view of and access to the operating field in the performance of a mini-cholecystectomy procedure.

DESCRIPTION OF THE PREFERRED EMBODIMENTS

Figure 1:
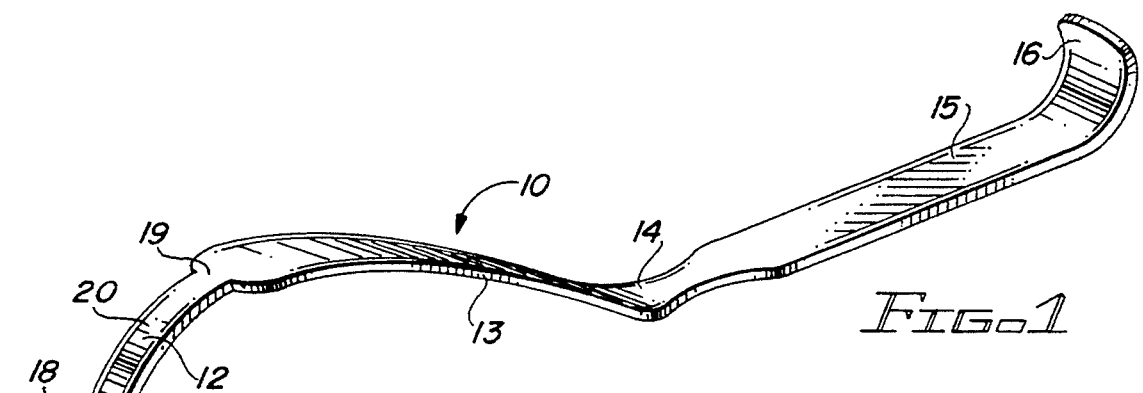
FIG. 1 is an isometric view of a surgical retractor embodying the present invention.

The present invention comprises a surgical retractor for use in mini-cholecystectomy surgical procedures and is identified by the general reference 10 in the accompanying drawings.

Retractor 10 comprises a head portion 11, a curvilinear neck portion 12, an elongated first body portion 13, a narrowed intermediate portion 14, an elongated second body portion 15, and a tail portion 16 as shown in FIGS. 1–6 inclusive.

Figure 3:
FIG. 3 is a plan view of the surgical retractor of FIG. 1.

One embodiment of device 10, as shown in FIGS. 1, 3 and 5, comprises a thin flat general rectangular head portion 11 angularly disposed relative to generally elongated body portion 13 and integrally secured thereto by a neck portion 12. As shown, neck portion 12 comprises a lead edge 18, and a trailing edge 19 integrally interconnected by a bend portion 20. The angle defined between a projection of edges 18, 19 is generally acute and will lie between about 75° to about 95°.

Edge 19 is integrally formed to elongated first body portion 13 and defines a smoothly curved planar surface 21 which effectuates the transition between neck portion 12 and the wider body portion 13.

In one practice of the present invention, head portion 11 will be provided with an axial length of approximately 5 cm and its width will vary between from about 3 to about 4 cm in size while the span along neck portion 12 between edge 18 to edge 19 will vary between from about 5.5 cm and 6 cm. The thickness of the several portions of retractor 10 is uniformly at 0.2 cm. The preferred width of neck portion 12 is 0.7 cm. The preferred width of intermediate portion 14 is from about 1.5 cm to about 2 cm to provide a finger grip region.

Figure 2:
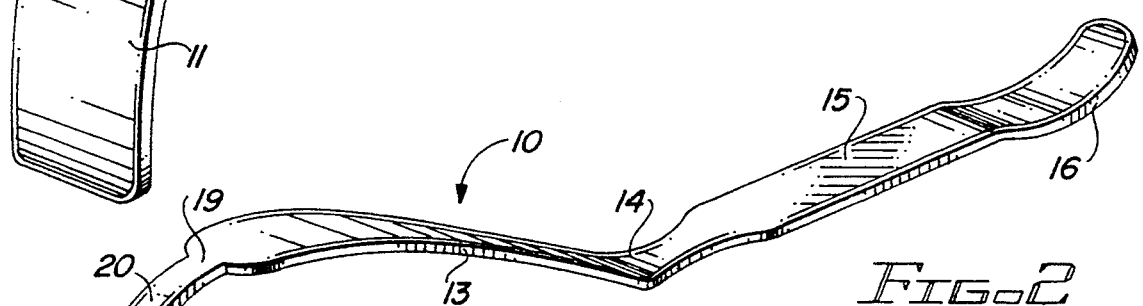
FIG. 2 is an isometric view of another surgical retractor embodying the present invention.
Figure 4:
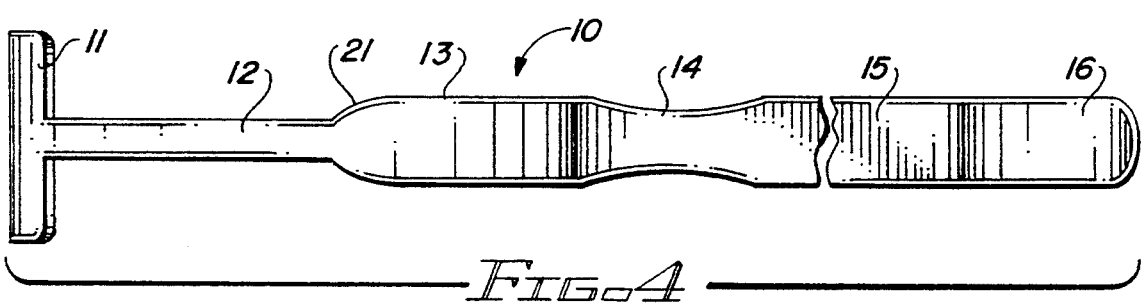
FIG. 4 is a plan view of the surgical retractor of FIG. 2.

Tail portion 16 has two preferred variations as are shown in FIGS. 1 and 2. As will appear, the choice of which variant is used is dictated by the exigencies of the particular surgical procedure being performed. Thus, in one version, as shown in FIGS. 2 and 4, tail portion 16 is disposed at a slight angle from the central longitudinal axis of second body portion 15. In practice, this angle will vary from about 20° to about 30°.

In the second variant as shown in FIGS. 1 and 3, tail portion 16 is disposed in almost orthoganal relationship to second body portion 15 and defines a hook-like appendage extending outwardly from about 2 cm to about 3 cm from the plane of body portion 15. The preferred width of body portions 13 and 15 and tail portion 16 is 2.5 cm.

In order to more fully understand the function retractors 10 embodying the present invention, let us consider their use within the environment of a cholecystectomy operation.

Prior to the surgery in which a retractor 10 embodying the present invention is employed, the patient 24 will be prepared for the operation using general anesthesia and appropriate muscle relaxation medication. Once in the surgical theater, a right subcostal, oblique skin incision 22 approximately four cm long beginning two cm from the midline of the abdomen is made in the patient. The fatty-subcutaneous layer is dissected and undermined over the anterior rectus sheath with approximately two (2) cm circumference of skin incision to provide full mobility. The anterior rectus sheath is then cut and the medial portion of rectus muscle is split between muscular septum with partial transection of muscle bundles. The posterior rectus sheath is cut, the peritoneum opened, the gallbladder palpated and elevated into the wound with a Kelly Clamp and emptied completely using a suitable evacuator such as a #16 needle trochar. The patient is then placed in a head up position with two (2) inch width vaginal gauze packed into the subhepatic space toward hepatic flexure of the colon and hepatico-gastric space.

A separator 10 of the type shown in FIG. 1 (designated as 10 (A) in FIG. 7) is then placed into the incision in such a manner that head portion 11 is positioned within the wound over the hepatico-gastric space, while neck portion 12 exits the wound. A separator 10 of the type shown in FIG. 2 (shown as 10 (B) in FIG. 7) is then placed so that its rectangular head portion 11 is disposed inside the incision under the surface of the liver to expose the Triangle of Calot. The neck portion 12 of device 10 (B) likewise extends out of the incision. With the two retractors embodying the present invention so positioned within the incision to completely expose the surgical field, the cystic artery is identified, ligated with clips and severed. The second separator 10 (B) is then removed from under the liver and placed with head portion 11 over the proximal hepatic duct area in hepatico-gastric space and neck portion 12 exits the wound while holding one side of the incision in an open position. Simultaneously, the first separator 10 (A) is repositioned so that head portion 11 is disposed over the duodenum to expose the cysto-hepatic area. Neck portion 12 of retractor 10 (A) also exits the wound and holds open the other side of the incision. With the complete surgical area fully exposed, the gallbladder is removed from the fundus down to the cystic duct by blunt and sharp dissection. With the use of the present invention, maximum exposure of the surgical field is achieved with a small incision, thus decreasing invasiveness of the surgery, decreasing operation time and cost, and substantially reducing patient recovery time.

After electro-coagulation and SURGICEL have accomplished the hemostasis in the gall-bladder bed, the patient is returned to a reclining, flat position and the vaginal gauze packing is removed. A suitable local anesthetic, such as MARCAINE, is infiltrated into the peritoneum and fascia layers, followed by closure. During this process, the slightly curved tail portion 16 of the separator 10 (B) (See: FIG. 6) would be further used with a small patient to elevate the liver surface while the severely angled tail portion 16 of retractor 10 (A) (See: FIG. 5) would be used with an obese person to elevate the fatty layer during closure of fascia.

From the foregoing, it becomes apparent that a new and useful devices have been herein described and illustrated which fulfill all of the aforestated objectives in a remarkably unexpected fashion. It is, of course, understood that such modifications, alterations, and adaptations as may readily occur to an artisan having the ordinary skills to which this invention pertains are intended within the spirit of the present invention which is limited only by the scope of the claims appended hereto.

Accordingly what is claimed is:

1. A surgical separator for assisting in mini-cholecystectomy procedures conducted through a right, subcostal oblique skin incision approximately four cm. long, said separator comprising a thin flat rectangular head portion adapted to be inserted through said incision, a first flat elongated body portion, a flat, elongated neck portion operatively interposed between said first body portion and said head portion and secured thereto to support said head portion in a continuous, smoothly curved angular relationship to said first body portion, said flat, elongated neck portion adapted to exit said incision and hold a side of said incision open, said flat, elongated neck portion being narrower than said head portion to provide maximum exposure through said incision, a flat second elongated body portion, a flat tail portion integrally formed with said second body portion and disposed at an angle relative to the longitudinal axis of said second body portion and extending therefrom; and a flat intermediate portion operatively interposed between said first body portion and said second body portion and integrally formed therewith, said flat intermediate portion being narrower than said first and second body portions.

2. A surgical separator according to claim 1 in which said tail portion defines an angle of from about 20° to about 30° with the longitudinal axis of said second body portion.

3. A surgical separator according to claim 1 in which said first body portion is flat and has a width of not more than 2.5 cm.

4. A surgical separator according to claim 3 in which said tail portion defines an angle of from about 20° to about 30° with the longitudinal axis of said second body portion.

5. A surgical separator according to claim 3 in which said tail portion defines an angle of from about 75° to about 95° with the longitudinal axis of said second body portion.

6. A surgical separator according to claim 1 in which said tail portion defines an angle of from about 75° to about 95° with the longitudinal axis of said second body portion.

7. A surgical separator according to claim 1 in which said angular relationship between said head portion and said first body portion is from about 75° to about 95°.

8. A surgical separator according to claim 7 in which said body portion is flat and has a width of not more than 2.5 cm.

9. A surgical separator according to claim 8 in which said tail portion defines an angle of from about 20° to about 30° with the longitudinal axis of said second body portion.

10. A surgical separator according to claim 8 in which said tail portion defines an angle of from about 75° to about 95° with the longitudinal axis of said second body portion.

* * * * *